(12) United States Patent
Shapiro et al.

(10) Patent No.: US 8,102,963 B2
(45) Date of Patent: Jan. 24, 2012

(54) CT SCANNER USING INJECTED CONTRAST AGENT AND METHOD OF USE

(75) Inventors: Olga Shapiro, Haifa (IL); David Ruimi, Ganot Hadar (IL); Rafi Brada, Hod-HaSharon (IL); Ehud Dafni, Caesarea (IL)

(73) Assignee: Arineta Ltd., Caesarea (IL)

( * ) Notice: Subject to any disclaimer, the term of this patent is extended or adjusted under 35 U.S.C. 154(b) by 299 days.

(21) Appl. No.: 12/418,678

(22) Filed: Apr. 6, 2009

(65) Prior Publication Data

US 2009/0252285 A1    Oct. 8, 2009

Related U.S. Application Data

(60) Provisional application No. 61/123,155, filed on Apr. 7, 2008.

(51) Int. Cl.
*A61B 6/00* (2006.01)

(52) U.S. Cl. .................................. 378/8; 378/9

(58) Field of Classification Search .................. 378/8, 9, 378/19, 91, 92, 95, 98, 98.2, 98.5, 114–116
See application file for complete search history.

(56) References Cited

U.S. PATENT DOCUMENTS

| 5,068,882 | A | 11/1991 | Eberhard |
| 6,760,399 | B2 | 7/2004 | Malamud |
| 6,782,071 | B1 * | 8/2004 | Tsuyuki ........................ 378/4 |
| 2006/0285633 | A1 | 12/2006 | Sukovic et al. |
| 2007/0258558 | A1 * | 11/2007 | Nishide et al. ................. 378/8 |

FOREIGN PATENT DOCUMENTS

| WO | WO 2006/038145 | 4/2006 |
| WO | WO 2008/122971 | 10/2008 |

* cited by examiner

*Primary Examiner* — Jurie Yun

(57) ABSTRACT

A CT scanner includes a first X-ray beam source, and a second X-ray beam source. With such an apparatus, first source is used to monitor buildup of an injected contrast agent in a selected region of interest relative to a patient and at least the second source is used to perform diagnostic scanning when the buildup of the contrast agent reaches a desired level.

31 Claims, 6 Drawing Sheets

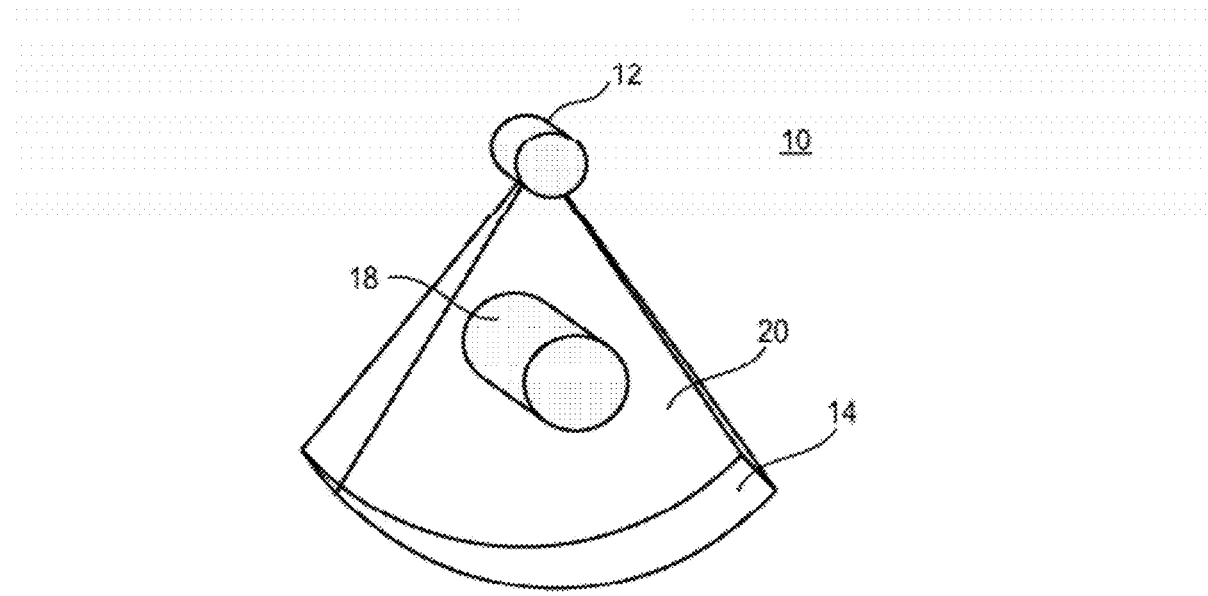
FIG. 1A   Prior Art
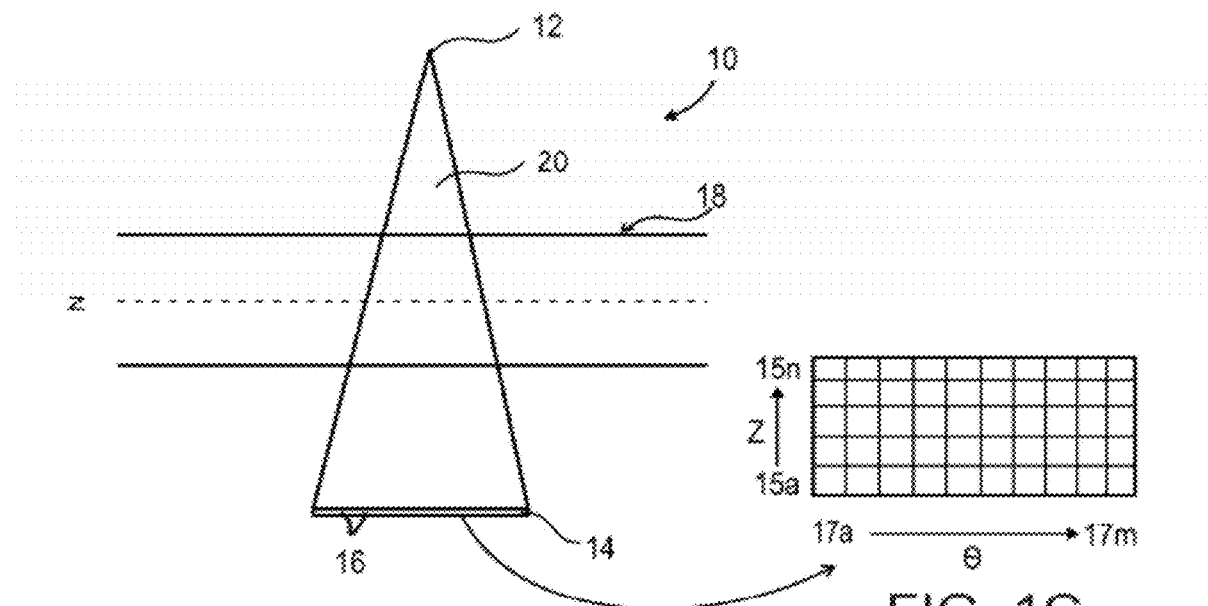
FIG. 1B   Prior Art
FIG. 1C

CT SCANNER USING INJECTED CONTRAST AGENT AND METHOD OF USE

RELATED APPLICATION

This application claims the benefit of U.S. Provisional Application 61/123,155, filed Apr. 7, 2008, the entire contents of which is incorporated by reference as if fully set forth herein.

FIELD AND BACKGROUND OF THE INVENTION

The present invention, in some embodiments thereof, relates to Computed Tomography (CT) scanners applied, by way of example, to imaging of the cardiovascular system. More particularly, the invention relates to CT scanning of subjects undergoing intravenous injection of a contrast enhancement agent.

A CT scanner typically comprises an X-ray source and detector system, both mounted on a gantry arranged to rotate about a scanned subject. Attenuation data are collected for X-rays that have traversed the scanned subject and impinged on the detector system. The data are then computer-processed (or reconstructed) to generate images of axial cross sections in the scanned subject or to form volumetric 3D images, to display the images and to store the images on computer media.

In some CT systems, the subject support is arranged to move in the direction of the axis of rotation relative to the rotating gantry to provide a spiral mode of operation. The availability of spiral mode, fast gantry rotation and large area detectors has led to the development of Computed Tomography Angiography (CTA) scanning whereby CT is used to image the human cardiovascular system with the aid of intravenous (IV) contrast agent injection. CTA scanning is also possible on cone beam CT scanners wherein the beam is wide enough to cover the organ of interest e.g. brain or heart. In cone beam scanners the imaging of the whole organ may be accomplished at a single patient position relative to the gantry.

The contrast agent is typically injected by a programmable power injector where the duration of injection, the volumetric rate of injection, and other parameters are adjusted according to the characteristics of the patient and the scan protocol. Nevertheless, the rate at which contrast agent concentration builds up at a particular blood vessel is variable from person to person because of different body size, weight and hemodynamic parameters. Since it is desired to perform the actual CT scan as near to the time of maximum contrast agent concentration as possible, the delay between start of contrast agent injection and the CT scan will vary from subject to subject. Therefore, it is customary to determine the optimal start time of the diagnostic scan relative to the start of injection for each subject individually.

According to one method known in the art as "test bolus", a preliminary injection of a small volume of contrast agent i.e., a test bolus, is used to determine the optimal timing. In this method the patient is injected with a small amount of contrast and a series of timed planar images are acquired in sequence at the same scan position. A region of interest (ROI) is graphically overlaid over a selected area of the image that exhibits contrast enhancement—for example, within the aorta—and the level of enhancement is determined as a function of time. The results are used to plan the delay between injection of the full required volume of contrast agent and the start of a subsequent diagnostic image data acquisition. Disadvantages of this method include the need for administration of additional contrast agent and the extra time and effort involved.

According to another method known in the art as "bolus tracking", the gantry is set in motion, and a planar image is generated at a selected gantry rotational position and an ROI is overlaid on the planar image at a given axial patient position where contrast enhancement is visible—again, for example, within the aorta. Injection is pre-programmed and administrated. While the injection goes on, the scanner is used to generate a series of planar images at the given rotational position and the level of enhancement in the ROI is monitored in almost real time. The actual diagnostic scan starts at a time determined by the measured enhancement. The timing is derived for example from the rate of increase of the enhancement level or the time at which the contrast agent level reaches a pre-set threshold or by some other algorithm. However, it takes several seconds to terminate the "bolus tracking" scan and revert to normal CTA scan operation since the patient typically must be moved to a different position relative to the scanner, a beam collimator must be readjusted, and new scan parameters must be loaded into the acquisition, reconstruction and X ray systems. Thus, the actual diagnostic scan does not start exactly at a determined optimal time but rather at some estimated time. As CTA scan times become shorter with modern CT scanners, it becomes more important to improve the scan timing relative to injection. Such improvement is also important to reduce the amount of contrast agent that needs to be administrated.

General background on coronary CTA, and on conventional contrast agent monitoring may be found in Jacobs, *How to Perform Coronary CTA. A to Z*, Applied Radiology, December 2006 Supplement, the content of which is incorporated herein by reference as if fully disclosed.

Known CT scanners having multiple displaced X-ray sources have been found to have utility in connection with the present invention. Examples include U.S. Pat. No. 5,068,882 to Eberhard, and U.S. Pat. No. 6,760,399 to Malamud and published applications US 2006/285633 A1 to Sukovic et. al. and WO 2006/038145 A to Koken et. al., show devices of this kind, and are incorporated herein by reference as if fully disclosed.

Published application WO 2008/122971 to Dafni (corresponding to U.S. application Ser. No. 12/307,374 filed 5 Jan. 2009) owned by the assignee of the present application, shows multiple beam scanner arrangements. This application is also incorporated herein by reference as if fully disclosed.

SUMMARY OF THE INVENTION

According to an aspect of some embodiments of the present invention there is provided a CT scanner comprising at least one first X-ray source and at least one second X-ray source, a detector arrangement adapted to receive radiation generated by the first and second sources; and a system controller which is operable to monitor build-up of an injected contrast agent utilizing radiation from the at least one first source detected by the detector arrangement in a selected region of interest of a patient, perform diagnostic scanning utilizing radiation from each second source, detected by the detector arrangement.

Optionally, the scanner further includes a third X-ray source, and the controller operates the third source in conjunction with the second source to perform diagnostic scanning.

Optionally, the controller operates one or more of the X-ray sources to perform a preliminary scan of the patient prior to injection of the contrast agent, and applies a graphical representation of the region of interest to a preliminary image resulting from the preliminary scan.

Optionally, the detector arrangement is comprised of a plurality of detectors, each respectively associated with one of the first and second X-ray sources.

Optionally, the detector arrangement is comprised of a single detector, controllably associated with all of the X-ray beam sources.

According to some embodiments of the invention, the detector arrangement is comprised of a plurality of matching relatively movable parts, each part respectively associated with one of the first and second X-ray sources.

Optionally, at least two of the detector parts are adapted to be arranged in abutting relationship.

According to some embodiments of the invention, the preliminary image and the scans for monitoring contrast level are planar scans.

According to some embodiments of the invention, the preliminary image and the scans for monitoring contrast level are rotational CT scans.

Optionally, the first and second X-ray beam sources are offset circumferentially about a scanner rotation axis.

Optionally, the first and second X-ray sources are spaced apart in a direction parallel to a scanner rotation axis.

According to some embodiments of the invention, the controller operates the first source in conjunction with the second source to perform diagnostic scanning.

According to some embodiments of the invention, the scanner further includes one or more adjustable collimators to direct the X-ray beams emitted by the sources to cover the required portions of the patient for contrast monitoring and diagnostic imaging. Optionally, each collimator is adjustable by the system controller.

Optionally, each first source emits an X-ray beam having low power relative each of the other sources when used for the preliminary and/or tracking scans, and high power when used for the diagnostic scan.

Optionally, each first source is a fan beam source and each second source is a cone beam source.

According to some embodiments of the invention, the X-ray beam sources are comprised of one or more of separate X-ray tubes, one or more vacuum enclosures with multiple anode and cathode pairs, and an X-ray tube that emits radiation from multiple focal points on the anode surface responsive to deflection of an electron beam.

According to an aspect of some embodiments of the present invention there is provided a method of performing CT scanning with an apparatus comprising first and second X-ray beam sources, the method comprising providing an injection of a contrast agent to a patient, monitoring the buildup of contrast agent in the patient in a selected region of interest using the first source, and performing diagnostic scanning of the patient using the second source when the monitored buildup of the contrast agent reaches a desired level.

Optionally, the method includes performing the diagnostic scanning using a third x-ray source in conjunction with the second source. Optionally, the diagnostic scanning is performed utilizing the first, second, and third sources. Optionally, the diagnostic scanning is performed utilizing the first and second sources.

According to some embodiments of the invention, the method further includes performing a preliminary scan of the patient prior to injection of the contrast agent, and applying a graphical representation of the region of interest to an image resulting from the preliminary scan.

According to some embodiments of the invention, the preliminary scan is performed using the first X-ray beam source.

Optionally, the preliminary image and the bolus tracking images are planar images. Alternatively, the preliminary image and the bolus tracking images are CT images.

Optionally, the method further includes adjusting the positioning of the first and second X-ray sources in a direction parallel to a scanner rotation axis.

Optionally, the method includes offsetting the X-ray sources circumferentially relative to each other about a scanner rotation axis.

According to some embodiments of the invention, the apparatus further includes one or more adjustable collimators, and the method further includes adjusting each collimator to direct the X-ray beams emitted by the sources to cover the required portions of the patient.

According to some embodiments of the invention, the method further includes adjusting the X-ray power to a lower level during said monitoring than during said diagnostic imaging.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1A is a simplified schematic illustration of a conventional cone beam CT scanner shown in perspective viewed generally axially;

FIG. 1B is a side view of the apparatus shown in FIG. 1A;

FIG. 1C is an enlargement in top view of the detector shown in FIG. 1B;

DESCRIPTION OF EMBODIMENTS OF THE INVENTION

Figure 2A:
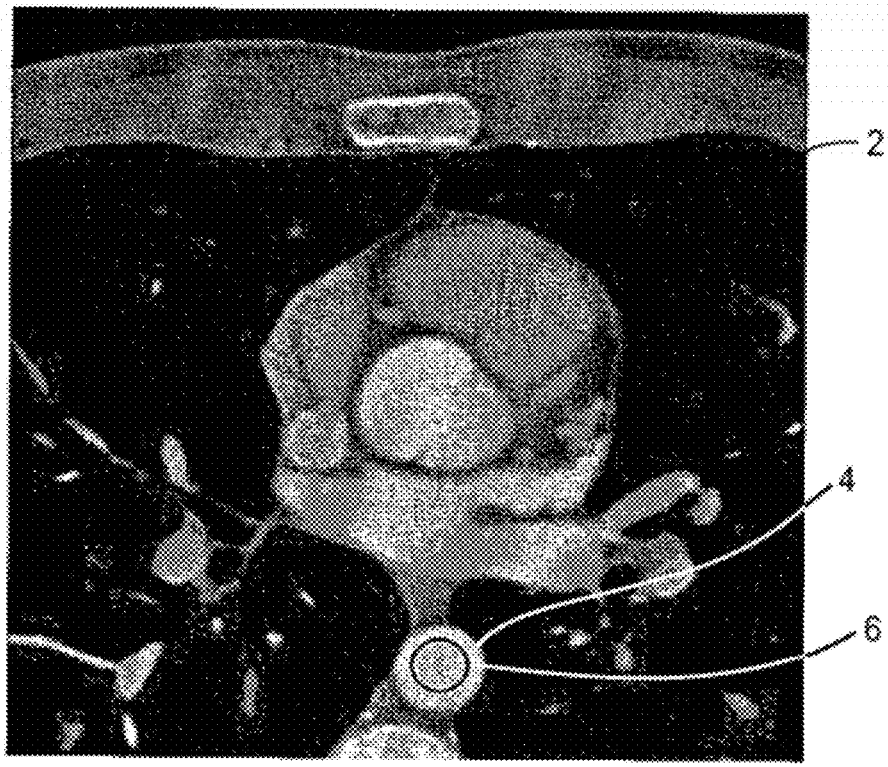
FIG. 2A illustrates a conventional axial CT image of the chest of a patient in which a graphical representation of a region of interest (ROI) has been superimposed on the aorta, within which contrast agent enhancement level is to be measured.

The present invention in some embodiments thereof, relates to Computed Tomography (CT) scanners applied, by way of example, to imaging of the cardiovascular system. More particularly, the invention relates to CT scanning of subjects undergoing intravenous injection of a contrast enhancement agent.

According to an aspect of some embodiments of the invention, multiple source CT scanners are used to achieve improved determination of optimum delay between the start of contrast agent injection and initiation of an actual diagnostic CT scan.

According to an aspect of some embodiments of the invention, with a CT scanner having multiple X-ray sources, a first one of the sources is used to monitor the buildup of contrast agent concentration in an ROI. When a desired contrast agent buildup has been achieved, buildup monitoring is terminated, and a normal diagnostic CT scan is performed using at least a second source, i.e., at least one source other than the one used for monitoring contrast build-up. Optionally, more than one source, optionally including, but not limited to the first source may be used to perform the diagnostic scan.

Optionally, a detector arrangement is provided in the form of multiple detectors, for example, area detectors, respectively associated with the multiple X-ray sources.

Optionally a single detector is controllably associated with the multiple X-ray sources.

According to an aspect of some embodiments of the invention, a preliminary planar or trans-axial image is acquired (without contrast agent) using the first source, i.e., the one used for contrast monitoring. A graphic region of interest (ROI) is then overlaid, optionally manually by the operator using a system master controller, on a portion of the preliminary image in which contrast agent buildup is to be monitored.

According to some embodiments of the invention, contrast buildup is monitored by acquiring a series of images from which the enhancement level in the ROI is determined in real time. This is sometimes referred to herein as "bolus tracking". When the detected enhancement level meets a predetermined condition, bolus tracking is terminated and a diagnostic CT scan is performed.

Optionally, the preliminary image and the scans for tracking contrast level are carried out at X ray beam intensity which is substantially reduced relative to the beam intensity used in the diagnostic scan. This feature is beneficial to reduce the over-all radiation dose applied to the patient.

Optionally, the sources are offset circumferentially about the rotation axis. Optionally alternatively or additionally, the source-detector pairs may be spaced apart in a direction parallel to the rotation axis.

In some exemplary embodiments, the X-ray beams emitted by the multiple sources are optionally adjusted by a master system controller to cover the required portions of the patient for bolus tracking and diagnostic imaging using adjustable collimators.

Optionally, the detector can be split into two or more parts movable relative to each other along the rotation axis.

For purposes of better understanding some embodiments of the present invention, reference is first made to the construction and operation of a conventional (i.e., prior art) CT scanner, as illustrated in FIGS. 1A-1C, and 2A and 2B of the drawings.

FIGS. 1A and 1B, are respectively a perspective view looking in a generally axial direction and a side view of a conventional cone beam scanner 10. Here, X-ray source 12 emits an X-ray beam 20 in the direction of a detector 14. Typically the source-detector pair is mounted on a rotating gantry (not shown) and a subject to be scanned, shown schematically at 18, is positioned on a movable platform (also not shown) between source 12 and detector 14. Detector 14 may be any array comprised of discrete elements 16 (see FIG. 1B) arranged in rows $15_a$-$15_n$, and columns $17_a$-$17_m$, (see FIG. 1C) or may be comprised of a flat panel detector or a detector employing any other suitable and desired technology. For the sake of simplicity, the gantry, subject support platform, and various other parts of the scanner are not shown throughout the drawings, as these parts are well known.

FIGS. 1B and 1C, show, conventionally, "rows" of the detector extending angularly in the θ direction into the plane of the paper, and columns extending in the direction of rotation of the gantry which carries source 12 and detector 14. It also shows columns of detectors extending in the Z direction, parallel to the axis of rotation.

Also conventionally, if the number of rows (n) in detector 14 is larger than 8 (or sometimes 16), the scanner is typically considered to be a cone beam scanner, while for smaller values of (n), the scanner is typically considered to be a fan beam scanner. Further general information concerning the relevant technology, and cone beam scanners in particular, may be found in the Dafni patent application and other reference sources mentioned above. Subject 18 can be scanned in any of several scan protocols known in the art: spiral, step-and-shoot or any other suitable and desired protocol. For CTA scanning, by way of example, the subject receives IV bolus injection and the beginning of the CTA scan is timed relative to the injection. As discussed above, prior art timing methods require a separate test bolus scan or adjustments of patient position and scan mode between a bolus tracking scans and the CTA scan, which limits the accuracy of timing.

Bolus tracking scans may typically be carried out in axial CT mode wherein the patient is at a fixed position relative to the gantry and axial CT images are acquired periodically while the gantry is rotating. Some exemplary embodiments of the present invention provide a first cone beam source and opposite wide detector such that planar radiographic images can be acquired at a fixed gantry angle. The gantry may be positioned so as to view a major artery, e.g. the aorta, in a planar image and the bolus tracking may be carried out by planar imaging rather than rotational CT imaging.

Figure 2B:
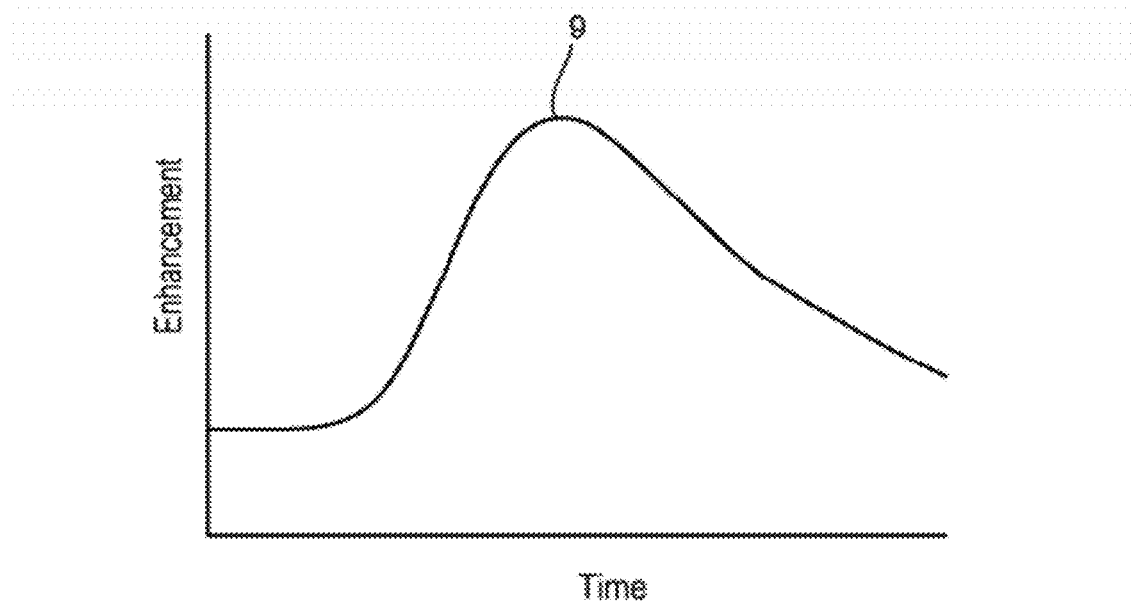
FIG. 2B is a graphical illustration of enhancement level versus time measured in the ROI from the start of bolus injection.

In FIG. 2A, at reference number 2, shows a typical trans-axial CT image in which the descending aorta is indicated at 4. Circle 6 represents an ROI graphically overlaid by the operator using the system controller on aorta 4. The ROI may be used for bolus tracking, i.e., to monitor the contrast enhancement level. FIG. 2B is a graphic representation of enhancement level versus time measured in the ROI from the start of bolus injection. The time to reach peak level 9 depends on the injection protocol as well as subject size, weight and hemodynamic parameters. In a typical bolus tracking application the enhancement may be measured every one second or every two seconds and the diagnostic scan may be initiated once the enhancement reaches a pre-set threshold.

Before explaining several illustrative embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 3:
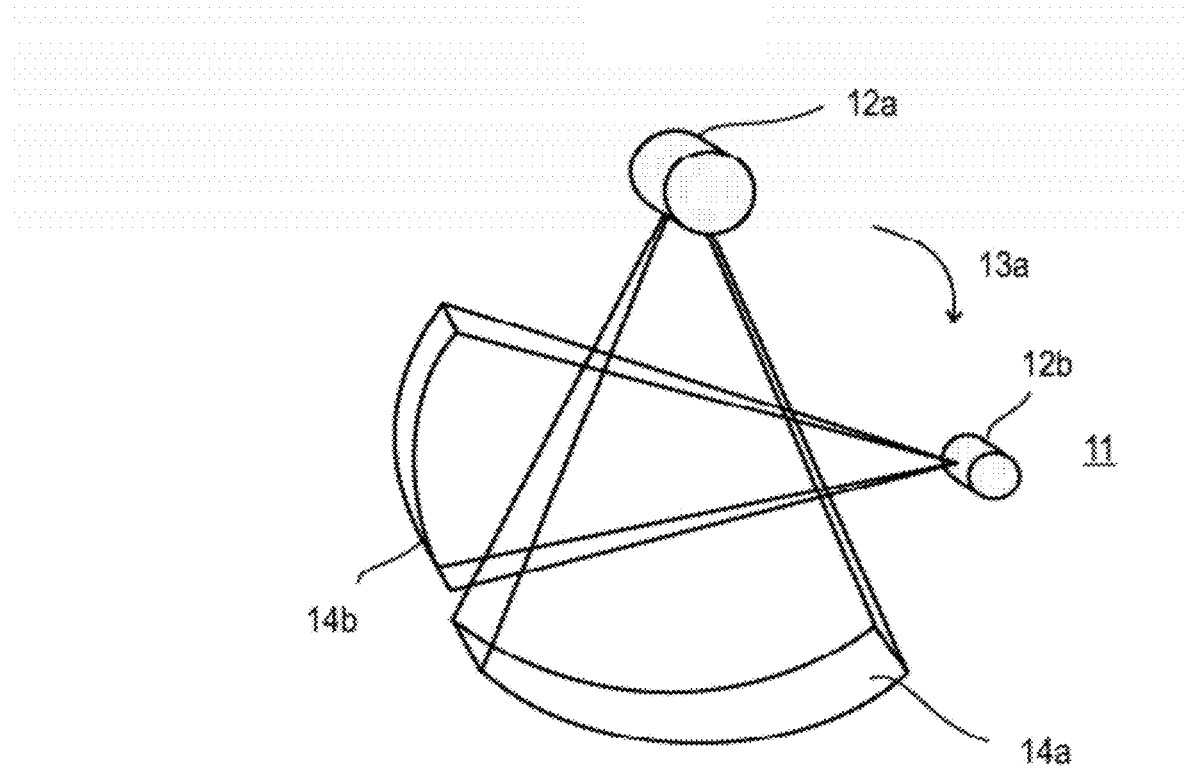
FIG. 3 is a simplified schematic illustration of the layout of a multiple beam scanner which is employed in accordance with some of the illustrative embodiments of the present invention.

FIG. 3 is a simplified graphical representation of the layout of a multiple beam scanner in accordance with some of the illustrative embodiments of the present invention. System 11 includes multiple X-ray sources 12a and 12b, and multiple detector arrays 14a and 14b respectively associated with the sources 12a and 12b. The number of rows in detectors 14a and 14b may optionally be such that that the device is a cone beam scanner or a fan beam scanner. As will be appreciated by those skilled in the art, beams 12a and 12b are shaped by suitable collimators (not shown) to match the configurations of the respective detectors 14a, 14b.

For simplicity, two sources 12a and 12b are shown with two associated detectors 14a and 14b. Sources 12a and 12b may be identical or different. Detectors 14a and 14b may likewise be identical or different. For example, source 12a and detector 14a may be adapted for cone beam imaging while source 12b and detector 14b may be adapted for fan beam imaging, wherein detector 14a comprises a large number of rows (e.g., 64 or 128 or 256) and detector 14b comprises of a small number of rows of detector elements (e.g., 1 or 2 or 4). Additionally, since 12b is used only for monitoring a small region of interest, the number of columns in 14b can also be reduced, especially if a planar image is used for monitoring, as described below.

The multiple sources and associated detectors in system 11 are shown as offset circumferentially about rotation axis Z, as indicated by arrow 13. Optionally, there may be no circumferential offset. Also optionally or additionally, the source-detector pairs may be spaced apart in a direction parallel to the Z axis. Such relative displacement of the source-detector pairs is advantageous where there is an axial offset between the region of interest for monitoring enhancement level and the region being diagnostically imaged. In the case of axial and/or rotational displacement of the source-detector pairs, the spacing and/or orientation between the source-detector pairs may optionally be fixed, or suitable means may be provided to move one or both of source-detector pairs 12a-14a and 12b-14b to different relative displacements or orientations. It should be noted that optionally, detector sections 14a and 14b may be constructed as separable relatively movable matching parts. In such an arrangement, if the two parts are positioned in abutting relationship, a single continuous detector array may effectively be obtained, as described below in connection with FIG. 8.

Further in regard to a detector with relatively movable parts, it should be understood that optionally, in some embodiments, only one of detector sections 14a and 14b is moveable, for example section 14a, or both detector sections 14a, 14b are movable. In some such embodiments, sources 12a and 12 are fixed relative to each other, and a collimator (not show) is used to direct the beam from source 12a onto detector section 14a, and the beam from source 12b onto detector section 14b. In any of these cases, the possible spacing between the detector sections and the corresponding configurations of the sources and/or collimator will be arranged to accommodate various applications.

Further, optionally, the beams from sources 12a and 12b may be collimated to be symmetric with respect to a plane perpendicular to the rotation axis and intersecting with the respective source or may be collimated to be asymmetric with respect to such plane.

Figure 4:
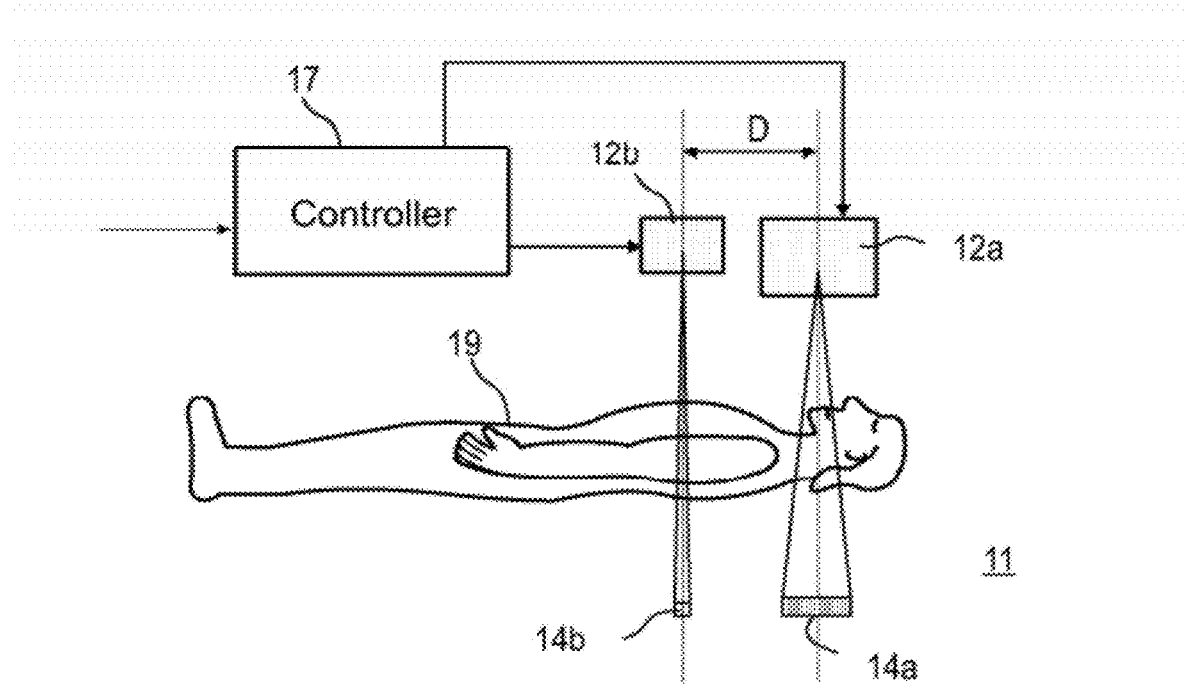
FIG. 4 is a side view of the scanner of FIG. 3 showing an illustrative embodiment of the invention.

FIG. 4 is a side view of system 11 as shown in FIG. 3, also showing a patient 19 undergoing a CT study, for example, a CTA study. In this exemplary embodiment, source-detector pairs 12a-14a and 12b-14b are displaced in the Z axis direction relative to each other by a distance D, chosen by a way of example, for a CTA study of the carotid arteries. For ease of visualization, the sources are shown in a same plane. As indicated in connection with FIG. 3, the source-detector pairs may be displaced azimuthally (circumferentially) or may be mounted at the same angle relative to the gantry (as shown in FIG. 4).

In a typical clinical application, the patient is positioned in the general scan volume and a planar image of the relevant body part is acquired. The planar image may be acquired by translation of the patient across the radiation field (known in art as scout scan), or if the beam angle and detector is sufficiently wide, by planar radiographic imaging using the system source and detector. The planar image is then used for fine positioning of the patient relative to the sources.

As will be understood by those skilled in the art, scanner 11 and the other exemplary embodiments described herein are operated by a master controller 17, which may be a suitably programmed general purpose computer, or multiple interconnected computers or a specially designed and constructed device, and suitable associated hardware. Master controller 17 is operable not only to control the position and operation of the sources and collimator but also other functionalities of scanner 11 or other exemplary embodiments. In particular it is operable to position a graphical ROI over the preliminary image, monitor and display in real time the contrast level and operate the algorithm for timing the start of the diagnostic scan.

In some embodiments according to FIG. 3 and FIG. 4 one source is used for bolus tracking scan. For example, in FIG. 4 source 12b is shown in position for bolus tracking measurement on the aorta of patient 19. In some embodiments a second source is used for the diagnostic CTA scan. For example, in FIG. 4 cone beam source 12a is shown in position for CTA scan on the carotid arteries of patient 19.

The use of a different X-ray beam source for diagnostic scanning and contrast agent monitoring according to various illustrative embodiments of the invention reduces the time delays in changing from one mode of operation (bolus tracking) to diagnostic CT scanning. In addition, the patent generally does not have to be moved between modes. Both of these lead to improved timing of the diagnostic CT scan at the onset of contrast and typically allow for injection of less contrast agent without loss of diagnostic information.

The timing for initiation of the diagnostic scan may be determined in any of several ways, for example, manually by an operator watching an on line updated enhancement graph such as shown in FIG. 2B, or by an automated algorithm monitoring the rate of contrast increase and leveling off, or any other suitable and desired method.

In the embodiment of FIG. 4, and in other exemplary embodiments of the invention described herein, reference is made to multiple X-ray beam sources. It is to be understood that the multiple sources may comprise one or more of (1) separate X-ray tubes (2) one or more vacuum enclosures with multiple anode and cathode pairs, (3) an X-ray that emits radiation from multiple focal points on the anode surface responsive to deflection of an electron beam and/or to any other method and apparatus known in the art for generation of X-rays from multiple emission points. Multiple sources share a high voltage generator in some of the exemplary embodiments and have a separate generator for each source in other embodiments.

In another example for application of system 11 of FIG. 4, a scan is performed on the renal arteries. In that case, the displacement D would be such that source detector pair 12a-14a is located closer to the patient's feet relative to source-detector pair 12b-14b instead of closer to the patient's head as in FIG. 4 to accommodate the fact that blood flows to the kidneys from above. In some exemplary embodiments the lateral distance D between the sources along the direction parallel to the rotation axis is fixed. In some exemplary embodiments the lateral distance may be adjusted according to application, with a corresponding adjustment in detector positions. In some exemplary embodiments, source-detector pair 12a-14a can be arranged to be moved past source-detector pair 12b-14b to reverse the orientation. In other exemplary embodiments, the patient would instead be positioned in the opposite direction relative to the scanner and the displacement D would be adjusted to the distance between the renal arteries and the desired bolus tacking position without changing the orientation of the source-detector pairs relative to each other.

Figures 5, 6:
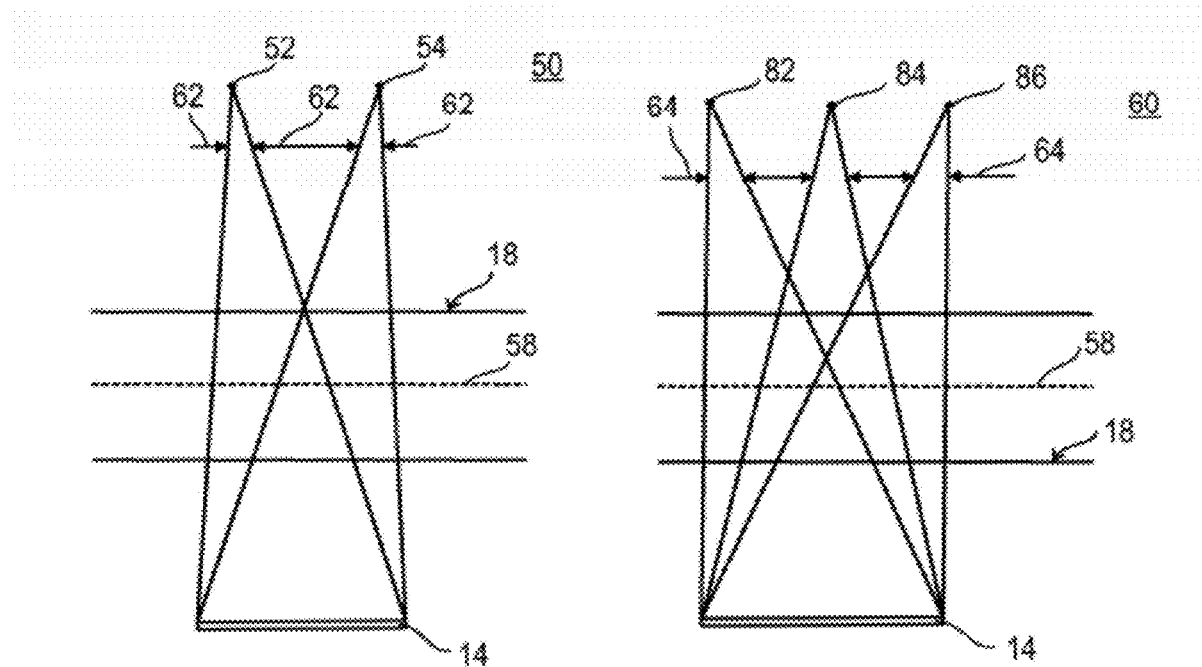
FIG. 5 is a simplified schematic illustration in side view of the layout of another multiple beam scanner, showing two beams, which is employed in accordance with some of the illustrative embodiments of the present invention.
FIG. 6 is a simplified schematic illustration in side view similar to FIG. 5 showing three X-ray sources.

FIG. 5 is a schematic side view showing the layout of another multiple beam scanner 50 having two beams, which is employed in accordance with some of the illustrative embodiments of the present invention. Scanner 50 comprises two cone beam sources 52, 54 spaced along line (not shown) which is parallel to the axis of rotation 58 (Z axis). The cone beams are collimated by a suitable collimator 62 so they traverse examination zone 18 and are directed onto single detector array 14.

Figure 7:
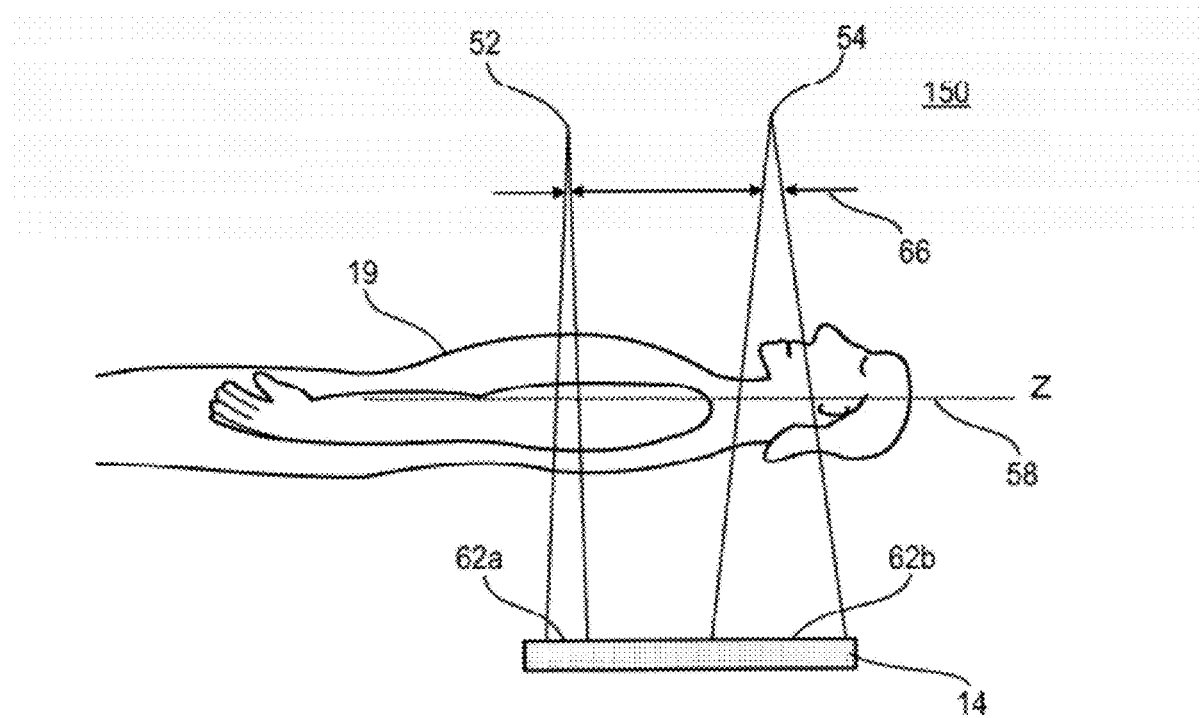
FIG. 7 is a simplified schematic illustration in side view of the layout of another multiple beam scanner showing two beams which is employed in accordance with some of the illustrative embodiments of the present invention.

FIG. 6 is a scanner 60 similar to scanner 50 in FIG. 5, but with three X-ray beam sources 82, 84, 86 collimated by a suitable collimator 64. Scanners such as 50 and 60 are advantageous in that they provide high coverage and reduced cone beam image artifacts. With the arrangements of FIGS. 5 and 6, the multiple cone beams may be fully or partially overlapping on detector 14 as shown, or may impinge on detector 14 in adjacent areas, optionally spaced apart as shown in FIG. 7 and described further herein below. In case of overlap of the beams on the detector area, the sources may be activated asynchronously so at any given time only one source is irradiating the detector.

The availability of three X-ray sources in the case of scanner 60 (FIG. 6) allows use of a first source for contrast monitoring, thus improving the timing of the diagnostic scan and the use of two different sources for the actual diagnostic scan, with consequent wide coverage without suffering from cone beam artifacts, as well as other benefits of dual source configuration.

As may be seen in FIGS. 5 and 6, detector 14 is used by all the X-ray beam sources. Using such an arrangement, for example, with the embodiment of FIG. 5, a master controller may be operative to adjust a suitable collimator 62 so that one source, e.g., source 54 is used only for diagnostic imaging, and one source, e.g. source 52 is used only for bolus tracking. Alternatively, only one source may be used for monitoring and both sources are used for diagnostic imaging. In embodiments wherein the tracking source is used also for diagnostic imaging, collimator 62 or 64 may be adjusted between the scans, so as to change the width of the beam from the tracking source, which still results in less delay than the delay between the tracking and diagnostic scans in prior art CT scanners. In the embodiment of FIG. 6, one of sources 82, 84 and 86 may be used for monitoring and one or more (preferably two or three) of sources 82, 84 and 86 may be used for the diagnostic scan.

Optionally, monitoring is performed with the collimators in their clinical imaging positions, so that no changes in the collimators are required when switching from monitoring to diagnostic imaging.

In either embodiment, a preliminary image (either CT or planar) is acquired without contrast agent using one of the sources and the common detector, and a graphic ROI is overlaid on the desired portion of the subject in the image, for example on the aorta. It should be recognized that in this and other embodiments, contrast sensitivity can be increased by subtracting the image without contrast from the monitoring image.

It should also be recognized that with collimators 62 or 64 adjusted before the preliminary scan, in some embodiments no time is lost due to adjustment when the optimum start time for diagnostic scanning has been determined. In embodiments or applications where adjustment of collimator 62 is made as described above, by proper relative positioning of the patient and the sources there will be no need to reposition the patient between the tracking and diagnostic scans.

Further information concerning the structure employed for the embodiments of FIGS. 5 and 6 may be found in the Dafni application referred to above. It is noted that while the outer beam profiles are shown as being asymmetric to optimize radiation utilization, conventional symmetric cone beams can be used.

FIG. 7 shows a scanner 150 according to another exemplary embodiment of the invention. System 150 is of similar construction to system 50 (FIG. 5) but X-ray beams 52 and 54 are shaped by a collimator 66 to irradiate different portions 62a and 62b of detector 14. These portions may be spaced apart as shown, or contiguous. Source 52 is used for example, for bolus tracking only and source 54 is used for CTA imaging only, with common detector 14 used to acquire data from either of the sources, each at the appropriate stage of the procedure. The X-ray beams emitted by sources 52 and 54 are adjusted to cover the required portions of the subject using an adjustable collimator 66. In exemplary embodiments adjustable collimator 66 is used to narrow the beam from source 52 for the bolus tracking stage and allows wider beam from source 52 for the CTA imaging such that both sources 52 and 54 are used in cone beam mode for the CTA.

In some exemplary embodiments of systems 50, 60 or 150 the lateral distance between the sources along the direction parallel to the rotation axis is fixed. In some exemplary embodiments the lateral distance between the sources may be adjusted according to application, with a corresponding adjustment in detector positions.

Figure 8:
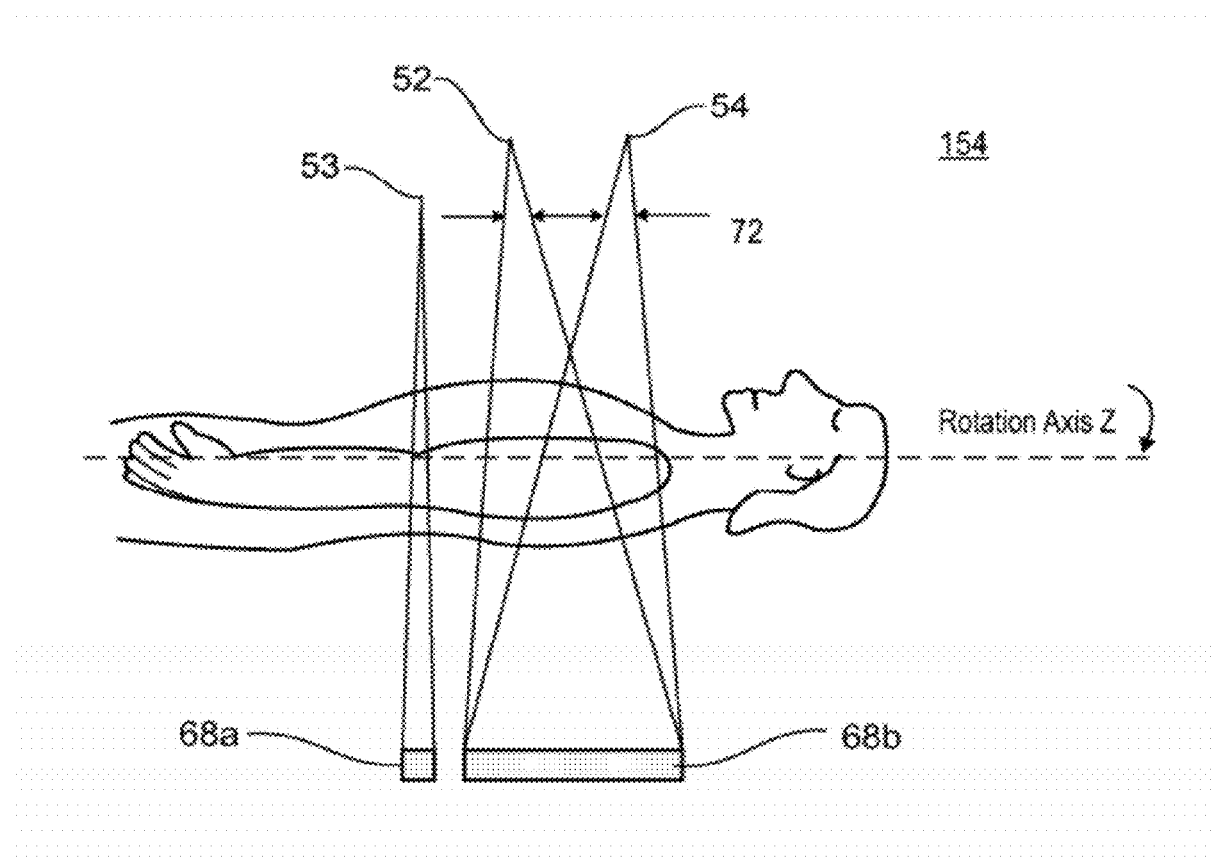
FIG. 8 is a simplified schematic illustration in side view of another three-beam scanner layout which is employed in accordance with some of the illustrative embodiments of the present invention.

FIG. 8 is another exemplary embodiment showing a system 154 having three X-ray sources 52, 53, and 54, and one or more suitable collimators 72. Here, for example, source 53 is used with detector section 68a for preliminary imaging and bolus tracking, and sources 52 and 54 are cone beam sources used in association with detector section 68b for diagnostic CTA scanning. Optionally, sources 52 and/or 54 may be used to obtain the preliminary image.

Figure 9:
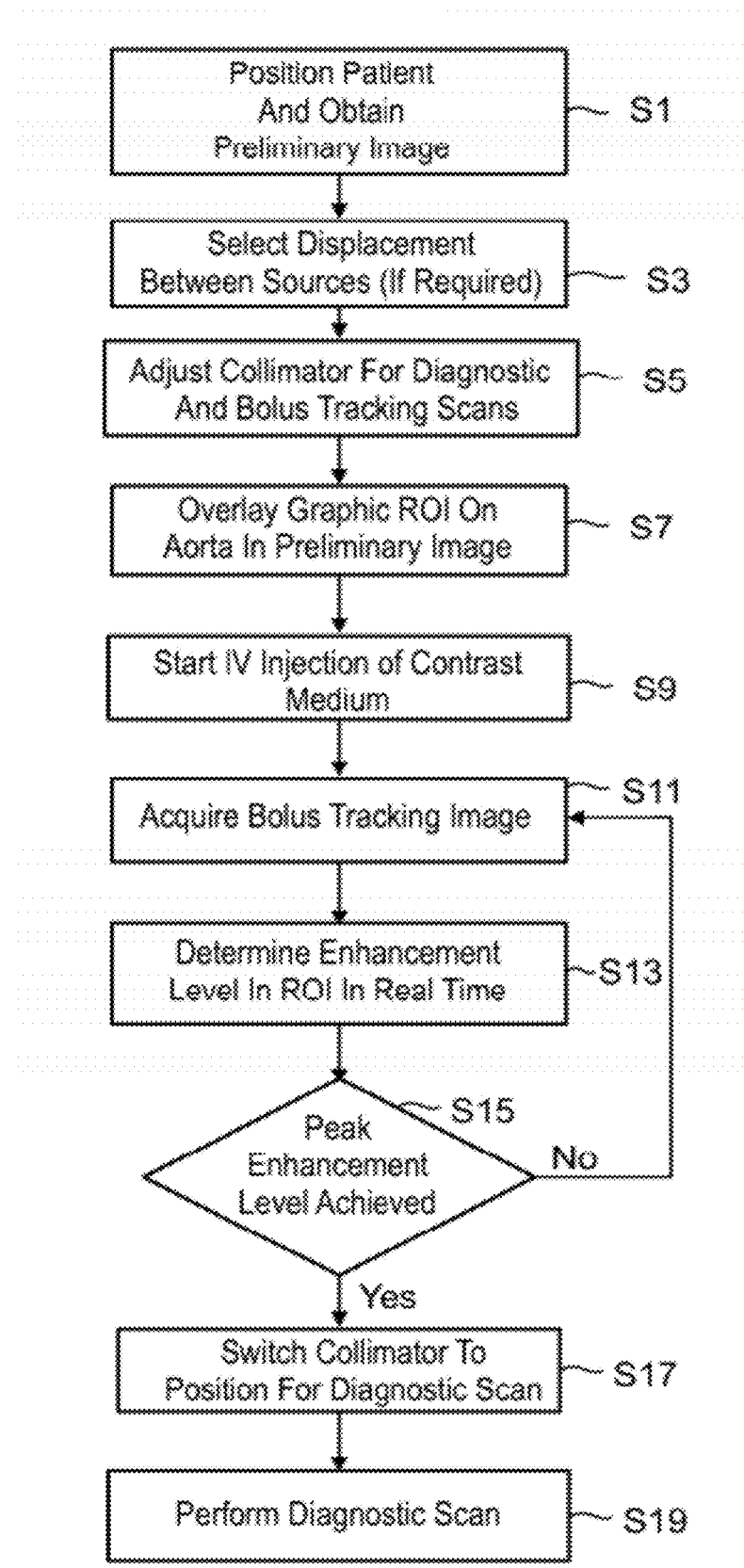
FIG. 9 is a flow diagram illustrating a mode of operation of the embodiments of FIGS. 3-8.

FIG. 9 is a flow chart illustrating operation of any of scanners 11, 50, 60, 150, and 154 shown in FIGS. 3-8 by way of example.

At S1, the patient is positioned in the system and a preliminary image is obtained. This may be a planar image obtained using by translation scanning or by using a cone beam and an area detector, or a CT image. The preliminary image is used to locate the monitoring ROI and CTA volume of interest.

At S3, the distance between the diagnostic and the monitoring sources is adjusted, where appropriate, for example in the embodiments of FIG. 4 and FIG. 7.

At S5, the collimator is adjusted, if required, such that one or more sources is positioned for the diagnostic scan and one or more sources is positioned for the preliminary scan and for bolus tracking. Then, at S7, a graphic ROI is overlaid over the region of interest, for example, the aorta, in the preliminary image in the manner previously described. In some embodiments of the invention the gantry has already been placed in rotation, and remains in rotation for the remainder of the process.

Thereafter, at S9, IV injection of the contrast agent is started according to the desired protocol. As the injection proceeds, radiation from the monitoring source is used to generate a series of bolus tracking images (at S11) and at S13, the enhancement level in the ROI is determined in real time.

In S15 a decision is made when to switch from tracking scans to diagnostic scan. As previously described, this may be done visually by the scanner operator watching an on line updated enhancement graph such as shown in FIG. 2B, or computed using any suitable algorithm. As non-limiting examples, such algorithms may comprise any of: (1) starting the diagnostic scan at a fixed delay after the enhancement level passes a pre-set threshold; (2) starting the diagnostic scan at a variable delay after the enhancement level passes a pre-set threshold, the delay depending on the slop of enhancement curve; (3) starting the diagnostic scan at a fixed delay after the slop of the enhancement curve reduces to a certain level; (4) starting the diagnostic scan as soon as possible when the enhancement curve levels at the a peak.

When a desired level of contrast enhancement is detected (S15), the collimator position is switched if required, as described above (S17). In case of a spiral scanner, the patient support is accelerated to linear motion. Then, at S19, one or more sources are used with the detector to produce the diagnostic CTA. If an enhancement decision to start the CTA scan has not been taken at S15, the process reverts to S11.

In some of the above exemplary embodiments, some of the x-ray sources are used for bolus tracking and one or more others are used for diagnostic imaging. In others, a source used for both tracking and diagnostic imaging, together with at least one other source. In some of the embodiments three sources are used. It should be understood that in many cases the functions of these sources can be interchanged. Thus, in a system in which one standard configuration, as described above, the bolus tracking is on one side of the diagnostic imaging (as for example for cardiac imaging), by interchanging the functions of the tubes from bolus tracking to diagnostic imaging, the system can be used for renal imaging without changing the positioning of the patient, which is sometimes inconvenient.

For purposes of interpretation of the above description and the following claims, it is to be understood that the terms "comprises", "comprising", "includes", "including" "having" and their conjugates mean "including but not limited to".

Further, as used herein, the singular form "a", "an" and "the" are specifically intended to include plural references unless the context clearly dictates otherwise. For example, in the claims, the term "an element" does not exclude the claim from encompassing more than one of such an element.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is also to be appreciated that for brevity, embodiments of the present invention are described without explicit reference to many components of CT systems known in the art but nevertheless such components are parts of the embodiments. These components comprise but are not limited to gantry, rotation system, high voltage generator, data acquisition system, means for image reconstruction, storage and display and at least one system controller.

It is also to be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

While several exemplary embodiments of the invention have been described in detail above, those skilled in the art will recognize other embodiments and variations which come within the scope of the invention. It is accordingly understood that the scope of the invention is not intended to be limited by the written description herein, but rather is to be given the full scope permitted by the following claims.

The invention claimed is:

1. A CT scanner comprising:
   at least one first X-ray source and at least one second X-ray source;
   a detector arrangement adapted to receive radiation generated by the first and second sources; and
   a system controller which is operable to:
   monitor build-up of an injected contrast agent utilizing radiation from the at least one first source detected by the detector arrangement in a selected region of interest of a patient;
   perform diagnostic scanning utilizing radiation from each second source, detected by the detector arrangement.

2. A CT scanner according to claim 1, further including at least one third X-ray source wherein the controller operates the at least one third source in conjunction with the second source to perform diagnostic scanning.

3. A CT scanner according to claim 1, wherein the controller operates one or more of the X-ray sources to perform a preliminary scan of the patient prior to injection of the contrast agent, and applies a graphical representation of the region of interest to a preliminary image resulting from the preliminary scan.

4. A CT scanner according to claim 3, wherein the preliminary image is a planar image and the preliminary scan is a planar scan.

5. A CT scanner according to claim 3, wherein the preliminary image and the preliminary scan are rotational CT scans.

6. A CT scanner according to claim 1, wherein the detector arrangement is comprised of a plurality of detectors, each respectively associated with one of the first and second X-ray sources.

7. A CT scanner according claim 1, wherein the detector arrangement is comprised of a single detector, receiving radiation from all of the X-ray sources.

8. A CT scanner according to claim 1, wherein the detector arrangement is comprised of a plurality of matching relatively movable parts, each part respectively associated with one of the first and second X-ray sources.

9. A CT scanner according to claim 8, wherein at least two of the detector parts are adapted to be arranged in abutting relationship.

10. A CT scanner according to claim 1, wherein the first and second X-ray sources are offset circumferentially about a scanner rotation axis.

11. A CT scanner according claim 1, wherein the first and second X-ray sources are spaced apart in a direction parallel to a scanner rotation axis.

12. A CT scanner according to claim 1, wherein the controller operates the first source in conjunction with the second source to perform diagnostic scanning.

13. A CT scanner according to claim 1, further including one or more adjustable collimators to direct X-ray beams emitted by the X-ray sources to cover the required portions of the patient for contrast monitoring and diagnostic imaging.

14. A CT scanner according to claim 13, wherein each collimator is adjustable by the system controller.

15. A CT scanner according to claim 1, wherein the at least first X-ray source used to monitor the build up of the injected contrast agent emits an X-ray beam at a lower power than the at least second X-ray sources used for the diagnostic scanning.

16. A CT scanner according to claim 1, wherein each first source is a fan beam source and each second source is a cone beam source.

17. A CT scanner according to claim 1, wherein the X-ray sources include at least one of one or more separate X-ray tubes, one or more vacuum enclosures with multiple anode and cathode pairs, and an X-ray tube that emits radiation from multiple focal points on an anode surface responsive to deflection of an electron beam.

18. A method of performing CT scanning with an apparatus comprising first and second X-ray beam sources, the method comprising:
providing an injection of a contrast agent to a patient;
monitoring the buildup of contrast agent in the patient in a selected region of interest using the first source; and
performing diagnostic scanning of the patient using the second source when the monitored buildup of the contrast agent reaches a desired level.

19. A method according to claim 18, and including performing the diagnostic scanning using at least one third x-ray source in conjunction with the second source.

20. A method according to claim 19 wherein the diagnostic scanning is performed utilizing said first, second and third sources.

21. A method according to claim 18 wherein the diagnostic scanning is performed utilizing said first and second sources.

22. A method according to claim 18, further including:
performing a preliminary scan of the patient prior to injection of the contrast agent; and
applying a graphical representation of the region of interest to an image resulting from the preliminary scan.

23. A method according to claim 22, wherein the preliminary scan is performed using the first X-ray beam source.

24. A method according to claim 22, wherein the image resulting from the preliminary scan is a planar image.

25. A method according to claim 22, wherein the image resulting from the preliminary scan is a CT image.

26. A method according to claim 18, further including adjusting the positioning of the first and second X-ray sources in a direction parallel to a scanner rotation axis.

27. A method according to claim 18 and including offsetting the X-ray sources circumferentially relative to each other about a scanner rotation axis.

28. A method according to claim 18, wherein the apparatus further includes one or more adjustable collimators, and wherein the method further includes adjusting each collimator to direct X-ray beams emitted by the X-ray sources to cover the required portions of the patient.

29. A method according to claim 18, wherein the method further includes adjusting X-ray power of the first X-ray source to a lower level during said monitoring than the second X-ray source during said diagnostic scanning.

30. A method according to claim 18 comprising generating a series of bolus tracking images from the first source.

31. The method according to claim 30, wherein the bolus tracking images are planar images.

* * * * *